US007377187B2

(12) United States Patent
Lai et al.

(10) Patent No.: US 7,377,187 B2
(45) Date of Patent: May 27, 2008

(54) AEROSOL SIZE-SELECTIVE IMPACTOR FOR REDUCING PARTICLE BOUNCE

(75) Inventors: Chane-Yu Lai, Shetou Township, Changhua County (TW); Sheng-Hsiu Huang, Jhongli (TW); Jia-Yun Lin, Taichung (TW); Chih-Chieh Chen, Taipei (TW)

(73) Assignee: Chung Shan Medical University, Taichung (TW)

( * ) Notice: Subject to any disclaimer, the term of this patent is extended or adjusted under 35 U.S.C. 154(b) by 327 days.

(21) Appl. No.: 11/225,063

(22) Filed: Sep. 14, 2005

(65) Prior Publication Data

US 2007/0056389 A1 Mar. 15, 2007

(51) Int. Cl.
*G01N 1/22* (2006.01)

(52) U.S. Cl. .................................................. 73/863.22

(58) Field of Classification Search .............. 73/863.22
See application file for complete search history.

(56) References Cited

U.S. PATENT DOCUMENTS

2002/0124664 A1* 9/2002 Call et al. ................ 73/863.22
2005/0153453 A1* 7/2005 Copeland et al. ............. 436/43
2005/0279181 A1* 12/2005 Trakumas et al. ....... 73/863.22

* cited by examiner

*Primary Examiner*—Robert Raevis
(74) *Attorney, Agent, or Firm*—Rosenberg, Klein & Lee

(57) ABSTRACT

An aerosol size-selective impactor for reducing particle bounce includes a main structure, a buffering layer, and a dehydration preventing layer. This main structure with an inlet and an outlet has a central channel and a receiving cavity. There are many nozzles in the inlet. The buffering layer is filled in the receiving cavity. The dehydration preventing layer is coated on the buffering layer for reducing the dehydration of water contained in the buffering layer. So, this invention utilizes the design of the receiving cavity to receive both layers. Its accuracy is high. Its sampling time lasts longer. It can endure vibrations. This invention can yield the particle bounce effect with lower cost. And, its application scope is wide.

2 Claims, 17 Drawing Sheets

AEROSOL SIZE-SELECTIVE IMPACTOR FOR REDUCING PARTICLE BOUNCE

BACKGROUND OF INVENTION

1. Field of the Invention

The present invention relates to an aerosol size-selective impactor for reducing particle bounce. Particularly, it relates to an aerosol size-selective impactor for reducing particle bounce that has a buffering layer and a dehydration preventing layer. It also utilizes the design of the receiving cavity to contain both layers. This invention has the advantages and functions as follows. Its accuracy is high. Its sampling time lasts longer. It can endure vibrations. It can minimize the particle bounce effect. Its cost is low. And, its application scope is wide.

2. Description of the Prior Art

In the past, the aerosol sampling at a working place or environment is to measure the total amount of the airborne aerosol particles. However, the hazardous aerosols will stay in different locations in human's breathing system. However, due to the size discrepancy of some aerosols, they will not reach the deeper area of the respiratory organ. For example, aerosols with a sufficiently large aerodynamic diameter having enough inertia force have little chance of entering the alveolar region of the lungs. Therefore, when a person measures the exposure amount of the ambient aerosols, the particle size distribution as a function of aerodynamic diameter should be considered. The respiratory tract can be treated as three regions: the head airways region, the tracheobraonchial region of the lungs including the trachea and ciliated airways, and the alveolar region of the lungs including non-ciliated airways and alveolar sacs. Using size-selective sampling recommendations as a basis, three fractions of the ambient airborne particles are defined: inspirable, thoracic and respirable.

These relate to airborne particles which can be expected to enter the head, lungs and alveolar regions of the lungs, respectively. The 50% cut-off size of the respirable, thoracic and inspirable fraction is 4 μm, 10 μm and 100 μm, respectively.

Based on the above-mentioned reasons, it is necessary to develop a size-selective impactor that can conduct a more precise aerosol sampling.

For the labor, the purpose for aerosol sampling at a working environment is to evaluate the health hazards associated with particles deposited in the human breathing system. For example, it can evaluate the mass concentration and size distribution of the airborne particles. An ideal size-selective sampler not only can provide a better aerosol sampling, but also can precisely evaluate the influence on human's health. The basic operation of a typical size-selective sampler is described below. Aerosols are passed through a nozzle and the output stream directed against a flat plate. The flat plate, called an impaction plate, deflects the flow to form an abrupt 90-degree bend in the streamlines. Particles whose inertia exceeds a certain value are unable to follow the streamlines and impact on the impaction plate. Smaller particles which can follow the streamlines and avoid hitting the impaction plate remain airborne and flow out of the impactor. All particles that impact on the impaction surface must stick on it without bounce. The particles collected from the impaction surface can be either chosen for subsequently analysis or discarded if treat impactor as a pre-classifier, for different sampling purposes and impactor designs.

Referring to FIG. 1, it is a traditional impaction substrate 90 that is coated with oil or grease. Practically, it is the silicone oil 91. This coating surface with oil or grease can increase the adhesion energy, the deformation and the dissipated energy (for the aerosols 92) on the surface of the impaction substrate 90. So, the dynamic energy of the moving particles can be reduced. It also can minimize the particle bounce problem. This kind of coating surface not only can reduce the particle bounce, but also can lower the particle loading effect.

As shown in FIGS. 2A and 2B, they illustrate the process when the moving aerosols 92 hit on the silicone oil 91. These aerosols 92 will stay inside the silicone oil 92. Because these aerosols 92 will not be dissolved in the silicone oil 91, they will stay and accumulate. When the loading of the hitting aerosols 91 exceed a certain level, as shown in FIG. 2C, the moving aerosols 92 will hit the prior laden aerosols 92 and bounce off eventually. This is the typical particle bounce problem. This particle bounce will significantly reduce the accuracy of the sampling data. Moreover, assuming that there are 1000 aerosols 92, only the first 500 aerosols 92 hit the silicone oil 91 and stay inside. So, the other 500 aerosols 92 will bounce away. Under such circumstance, the error or sampling bias of this measurement becomes extremely large.

Furthermore, the oil or grease used in the traditional size-selective sampler usually is the silicone oil 91. However, the silicone oil 91 cannot sustain long-term heavy particle loading as incoming particles are bouncing off particles that had already been deposited. Its sampling time cannot last too long. It is another disadvantage.

In addition, if the silicone oil 91 is replaced by another oil with low volatility, its viscosity is lower. So, it is very easy to leak out while this sampler is shaking, vibrating or tilting (especially when the person is walking). Consequently, the sampling result will be inaccurate.

SUMMARY OF THE INVENTION

The primary object of the present invention is to provide an aerosol size-selective impactor for reducing particle bounce. It utilizes the design of downward receiving cavity to contain the buffering layer and the dehydration preventing layer. Hence, its accuracy is high.

The second object of the present invention is to provide an aerosol size-selective impactor for reducing particle bounce. Its sampling time lasts longer. It also can achieve higher loading for particles.

The other object of the present invention is to provide an aerosol size-selective impactor for reducing particle bounce. It can endure vibrations, even for a walking labor who wears this impactor on.

Another object of the present invention is to provide an aerosol size-selective impactor for reducing particle bounce. Its cost is low and its application scope is wide.

In order to achieve the above-mentioned objects, a technical solution is provided. An aerosol size-selective impactor for reducing particle bounce, comprises:

a main structure having an inlet and an outlet, said main structure being disposed with an central channel and a receiving cavity, said inlet being disposed with at least one nozzle;

at least one buffering layer installed in said receiving cavity, said buffering layer containing water and being a semi-solid structure remaining a predetermined shape; and a dehydration preventing layer coated on said buffering layer for reducing a drying phenomenon of said buffering layer.

DETAILED DESCRIPTION OF THE PREFERRED EMBODIMENT

Figure 1:
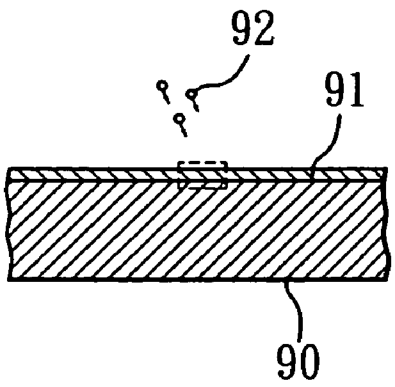
FIG. 1 illustrates a traditional impaction substrate.
Figure 2A:
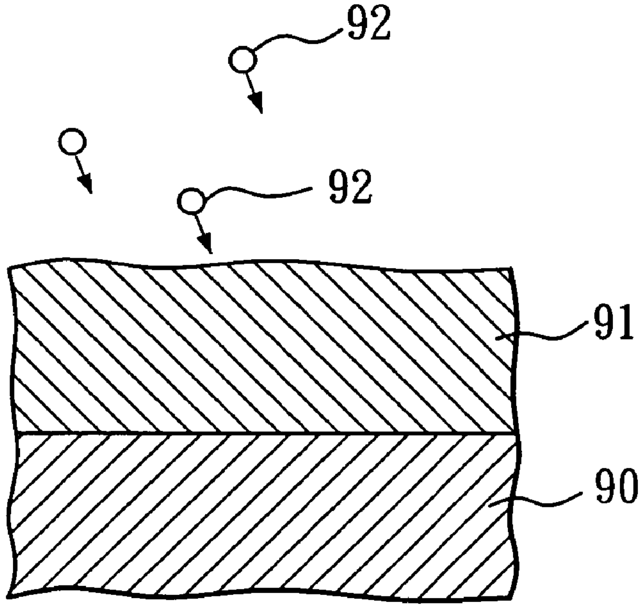
FIGS. 2A, 2B, and 2C show the moving process of the aerosols hitting on the traditional device at different stages.
Figure 2B:
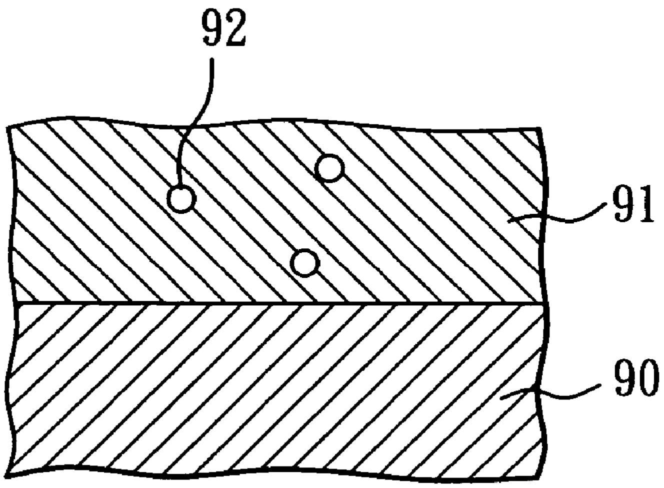
Figure 2C:
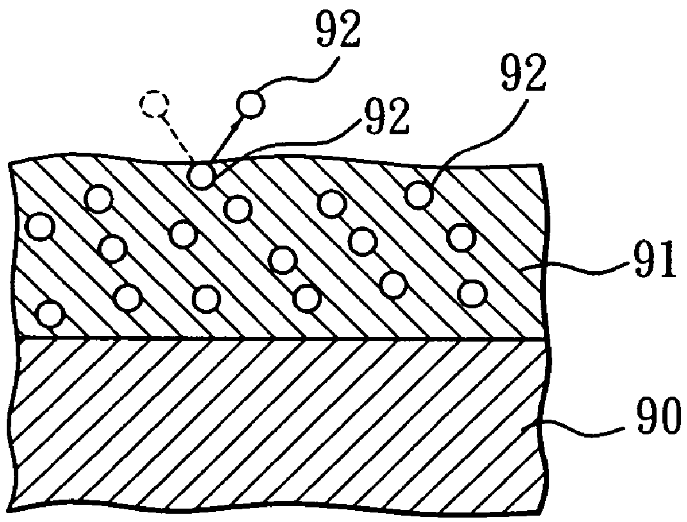
Figure 3:
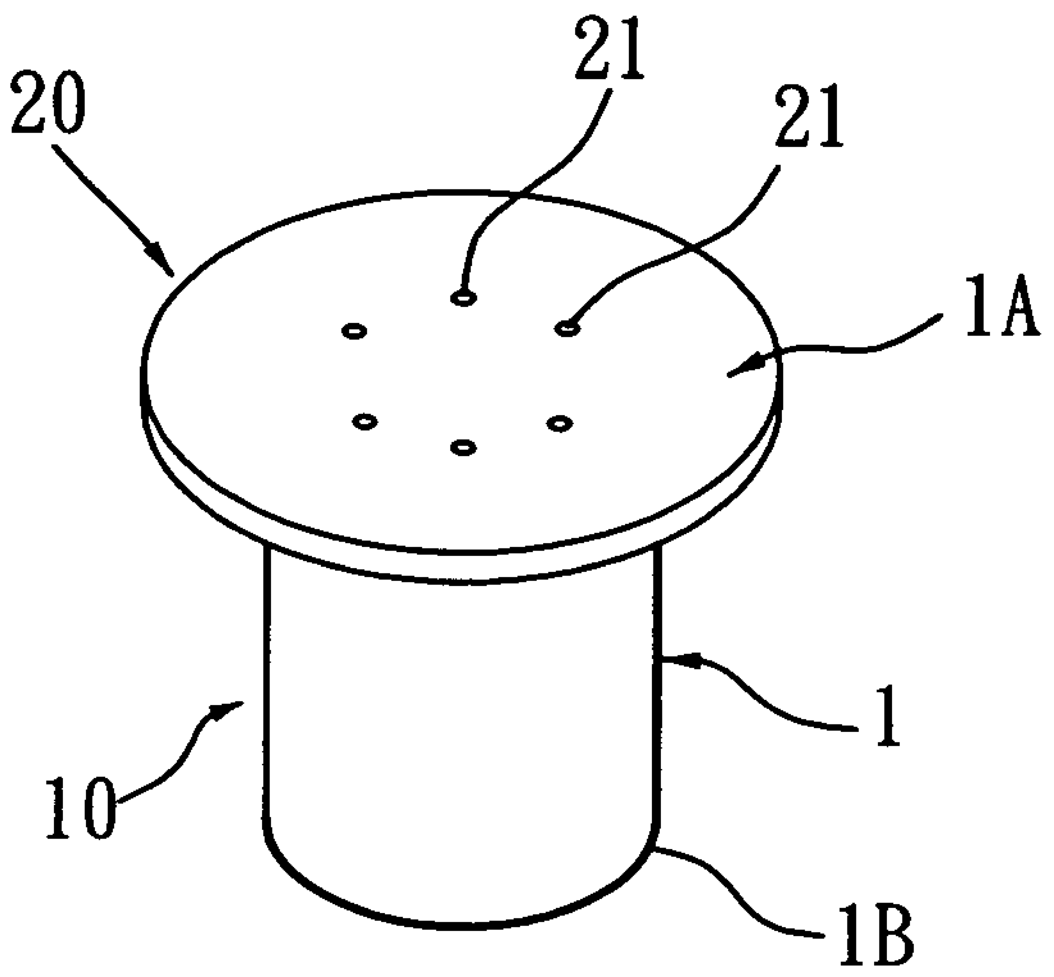
FIG. 3 is a perspective view of the present invention.
Figure 4A:
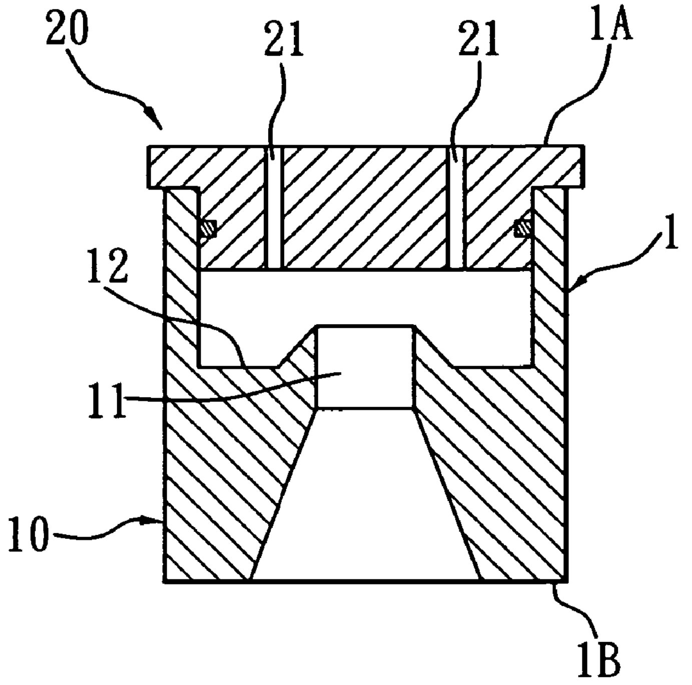
FIGS. 4A, 4B, 4C, 4D, 4E, 4F and 4G show different testing conditions of the present invention.
Figure 4B:
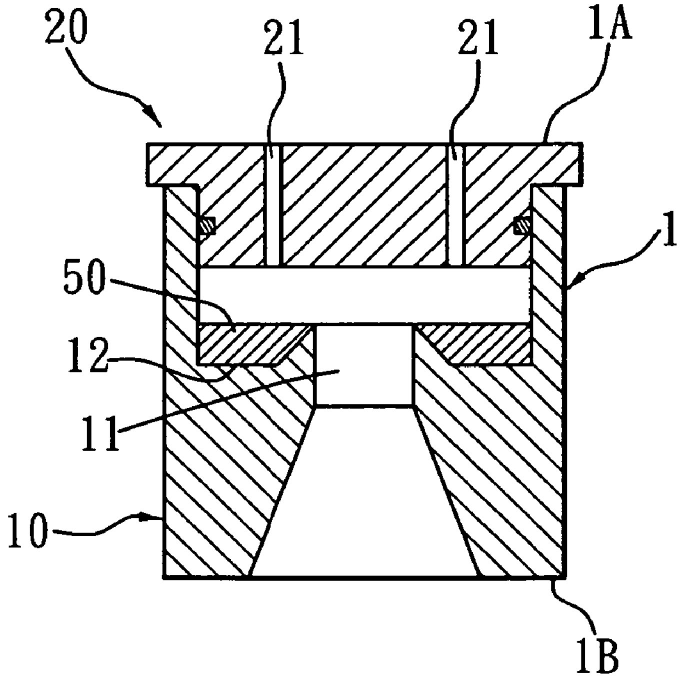
Figure 4C:
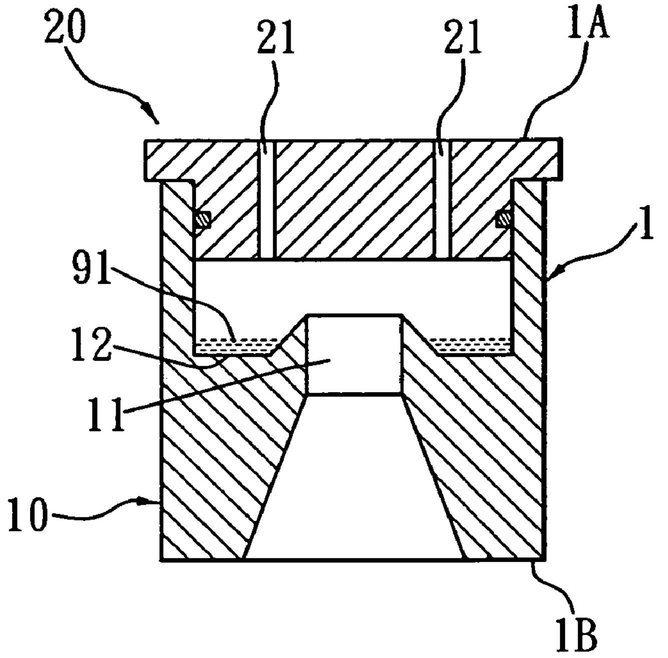
Figure 4D:
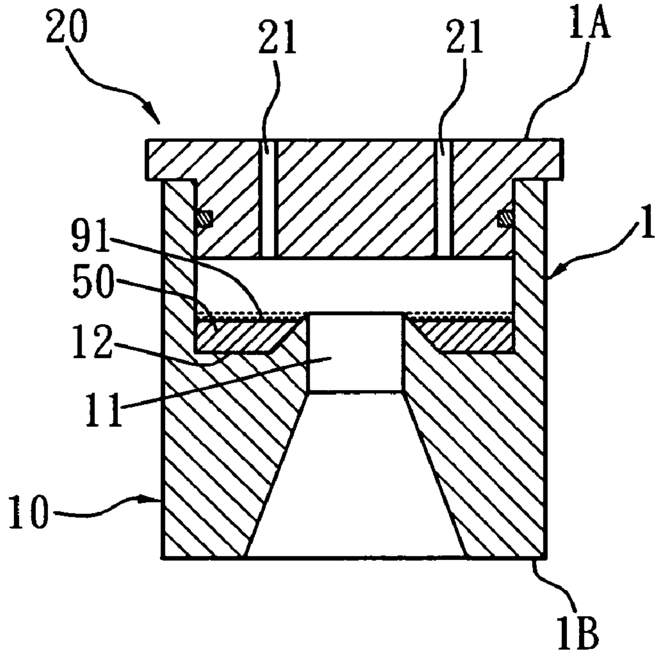
Figure 4E:
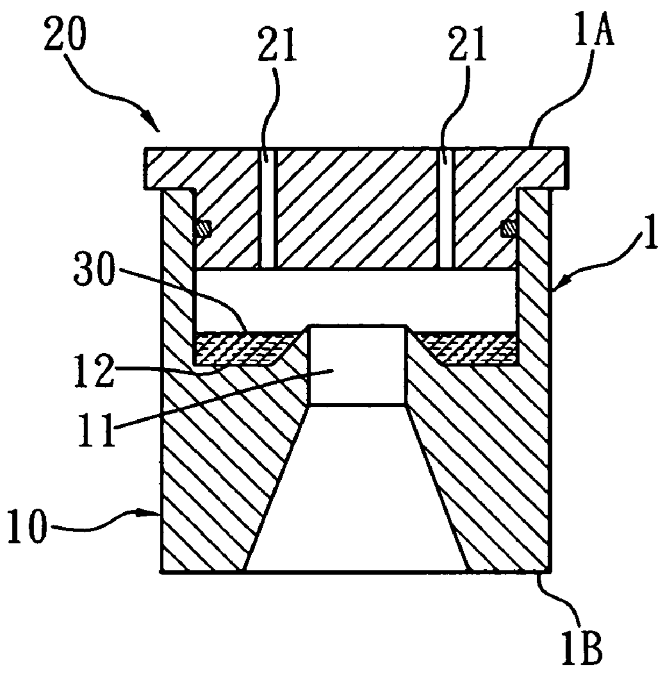
Figure 4F:
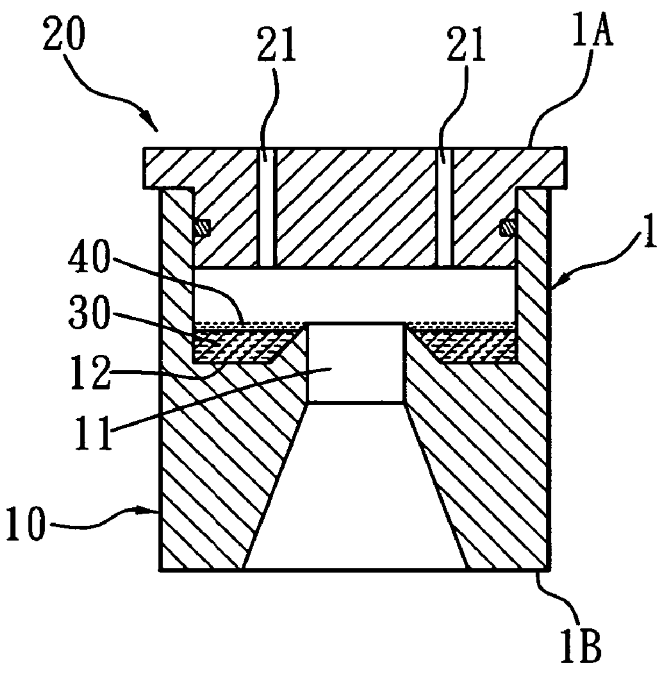
Figure 5:
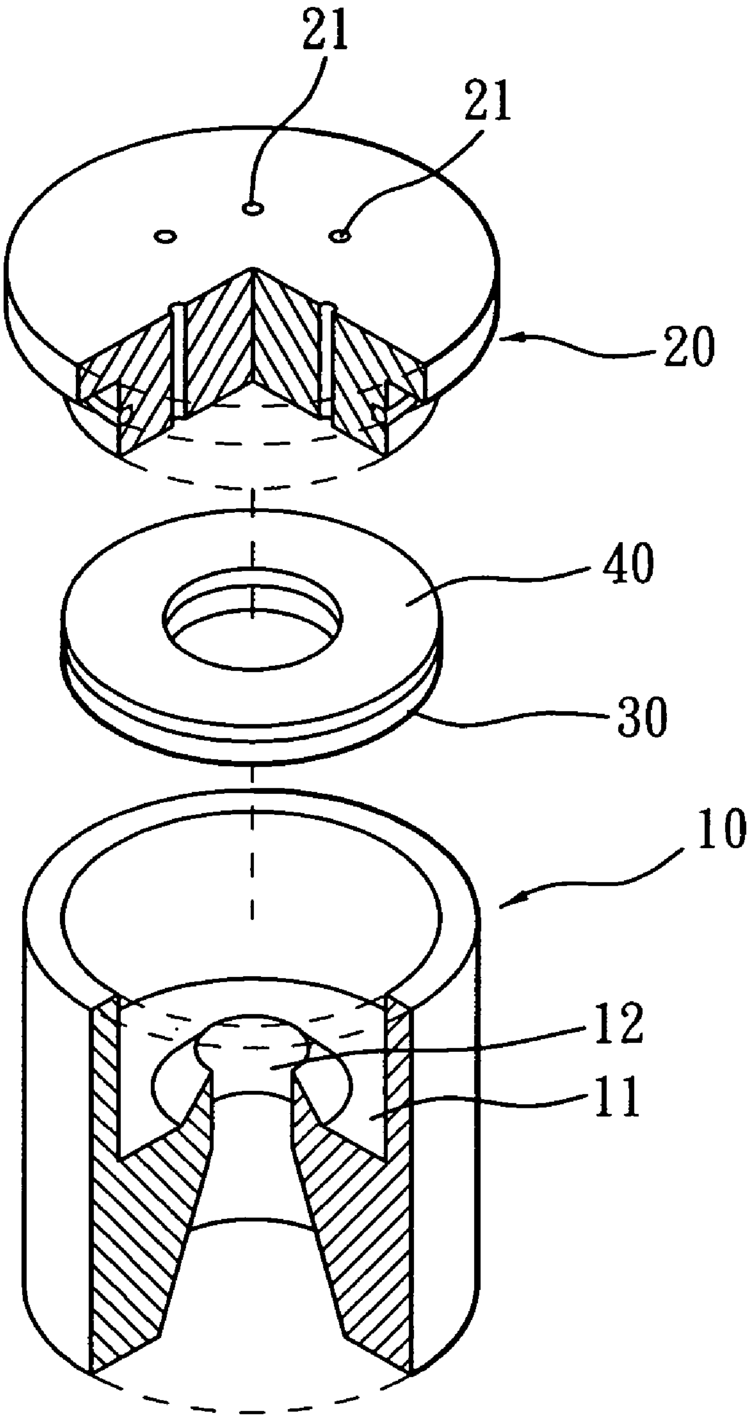
FIG. 5 is an exploded view of the present invention.

Referring to FIGS. 3, 4F and 5, the present invention is an aerosol size-selective impactor for reducing particle bounce. It mainly comprises a main structure 1, at least one buffering layer 30, and a dehydration preventing layer 40.

With regard to the main structure 1, it has an inlet 1A and an outlet 1B. This main structure 1 is disposed with a central channel 11 and a receiving cavity 12. The inlet 1A is disposed with one or more nozzles 21. Practically, this main structure 1 includes a base 10 and a nozzle plate 20 that can fit on the base 10. The central channel 11 and receiving cavity 12 are disposed on the base 10, and the nozzle plate 20 has one or more nozzles 21 thereon. Furthermore, the central channel 11 has a lower portion that is conical. For example, it can be shaped like a funnel structure or conical expander.

About the at least one buffering layer 30, it is installed in the receiving cavity 12. The buffering layer 30 contains certain water and is a semi-solid structure remaining a predetermined shape.

For this dehydration preventing layer 40, it is coated on the buffering layer 30 for reducing a drying phenomenon of the buffering layer 30. The dehydration preventing layer 40 is preferably selected from one of the group: silicone oil, low-volatile oil, low-volatile grease, and chemical material to preventing dehydration.

Figure 6A:
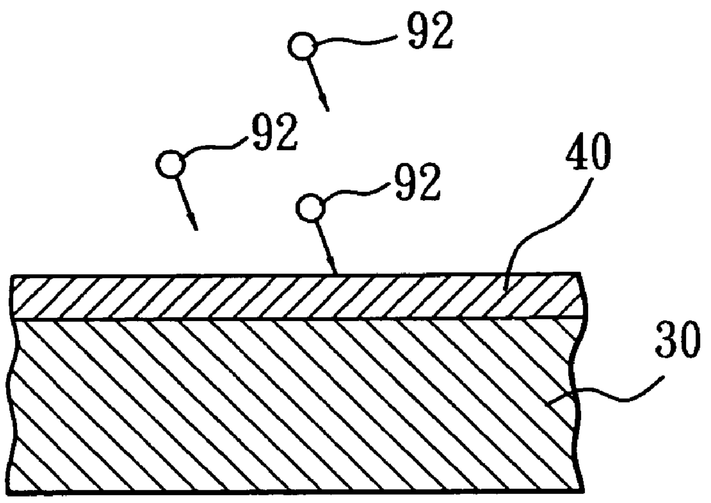
FIGS. 6A, 6B, 6C, and 6D show the moving process of the aerosols hitting on the present invention at different stages.
Figure 6B:
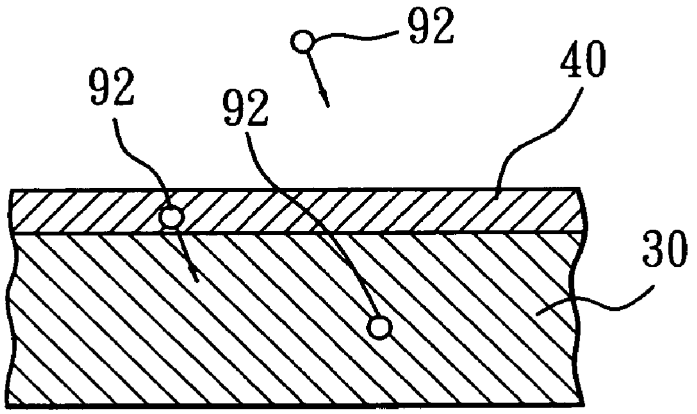
Figure 6C:
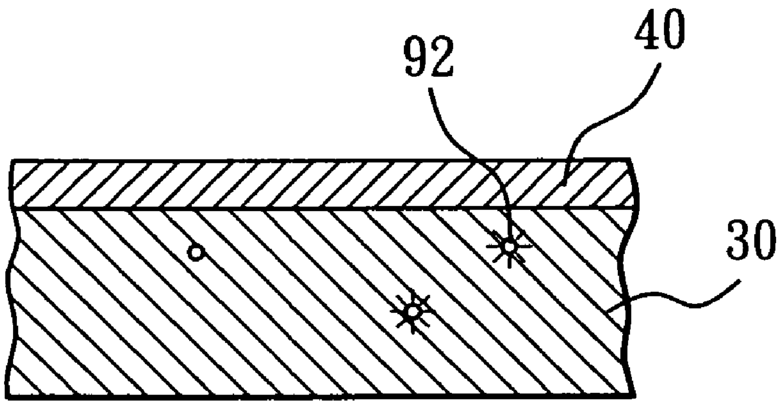
Figure 6D:
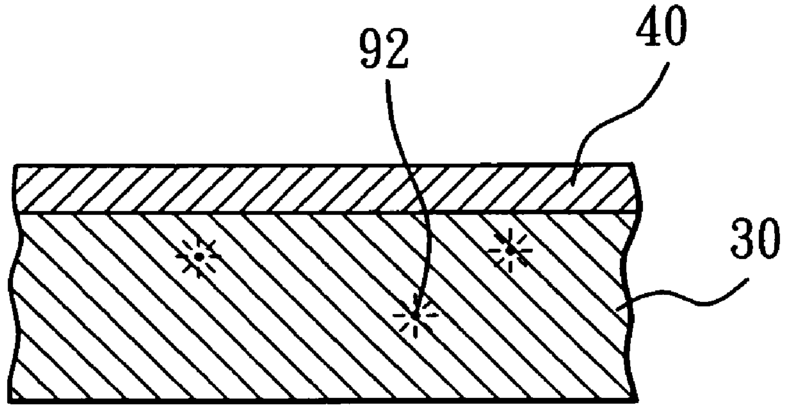

Concerning the detailed operation of this invention, it is achieved by the buffering layer 30 and the dehydration preventing layer 40. As illustrated in FIG. 6A, there are several aerosols 92 move into the dehydration preventing layer 40. These aerosols 92 penetrate the dehydration preventing layer 40 and enter the buffering layer 30 (as shown in FIG. 6B). Because the buffering layer 30 contains certain water. These water-soluble aerosols 92 will gradually be dissolved into water, as shown in FIG. 6C. Finally, all of them are complete dissolved into water as exhibited in FIG. 6D. That is, under the capacity of this buffering layer 30, even though there are new aerosols 92 moving in, they still can be received and dissolved. Therefore, no particle bounce problem occurs.

In this preferred embodiment, the buffering layer 30 can be selected from Trypticase Soy Agar (briefly referred as TSA hereafter), other kind of Agar that contain water, glue, solid water-soluble material, grease that contains water, low-volatile oil that contains water, etc. In this embodiment, the silicone oil 91 is chosen.

Figure 7:
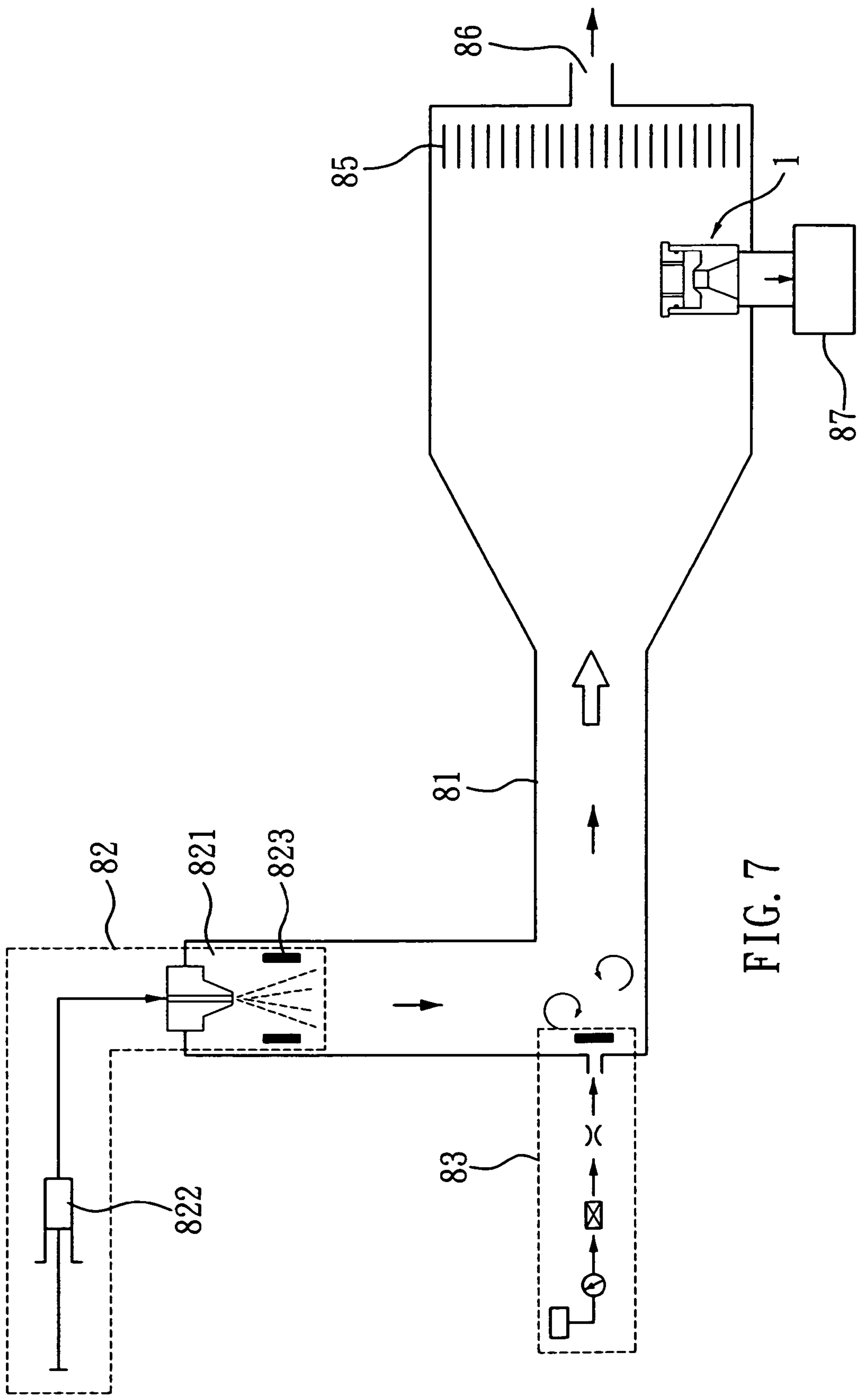
FIG. 7 is a schematic view showing the entire experimental equipment for the present invention.

Referring to FIG. 7, the entire experimental equipment include: a L-shaped pipe 81, a water-soluble aerosols generator 82, an electro-neutralizer 823, a air-stream generating device 83, a filter 85, an exhaust port 86 and an aerodynamic aerosol size detector 87 (such as aerodynamic particle sizer, or briefly called APS). The present invention is installed in the channel connecting to the aerodynamic aerosol size detector 87.

The water-soluble aerosols generator 82 is mounted in the upper left portion of the L-shaped pipe 81. It includes an ultrasonic atomizing nozzle 821, a fluid provider 822 (such as a syringe pump), and the afore-mentioned electro-neutralizer 823. The fluid provider 822 generates the required solvent. After which, this solvent is vaporized into small droplets in the air and then dehydrated or diluted to certain condition. So, the aerosols to be tested are formed. A 120 KHz ultrasonic atomizing nozzle generated the challenge aerosol particles. The count median diameter of the droplets generated by this generator was in the range from 15 μm to 20 μm, depending on the surface tension, viscosity of the solution, and the power output from the power supply. Because these airborne aerosols usually contain high level of static electricity, it is required to neutralize them by utilizing the electro-neutralizer 823. So, the testing results will not be influenced by the electricity carried by the aerosols. Plus, the entire experimental system will become more stable. By utilizing the electro-neutralizer 823, the electricity carried by the aerosols is neutralized to the Boltzmann charge equilibrium condition.

After which, these aerosols move downward and meet the air turbulence generated by the air-stream generating device 83. These aerosols continue to move toward the exhaust port 86. The filter 85 installed by the exhaust port 86 is used to filter the air flowing though. Some part of aerosols will be drawn to the aerodynamic aerosol size detector 87 via the present invention.

Besides, for the solid water-soluble particles, they can be Potassium Sodium Tartrate Tetrahydrate (briefly called PST hereafter). So, it can generate the particles (which are the aerosols 92) with wide-ranged size distribution and with high concentration.

The experimental results and analysis are described below (also see FIG. 8).

There are four kinds of conditions. The first one is only the empty receiving cavity 12 (such as FIG. 4A; its result is shown in curve L81 in FIG. 8). The second one is that a flat aluminum impaction plate 50 is horizontally mounted on the receiving cavity 12 (as shown in FIG. 4B; its result is shown in curve L82 in FIG. 8). The third one is that the receiving cavity 12 is coated with silicone oil 91 (as shown in FIG. 4C; its result is shown in curve L83 in FIG. 8). The fourth one is that an aluminum impaction plate 50 coated with silicone oil 91 and horizontally mounted on the receiving cavity 12 (as shown in FIG. 4D; its result is shown in curve L84 in FIG. 8).

Figure 8:
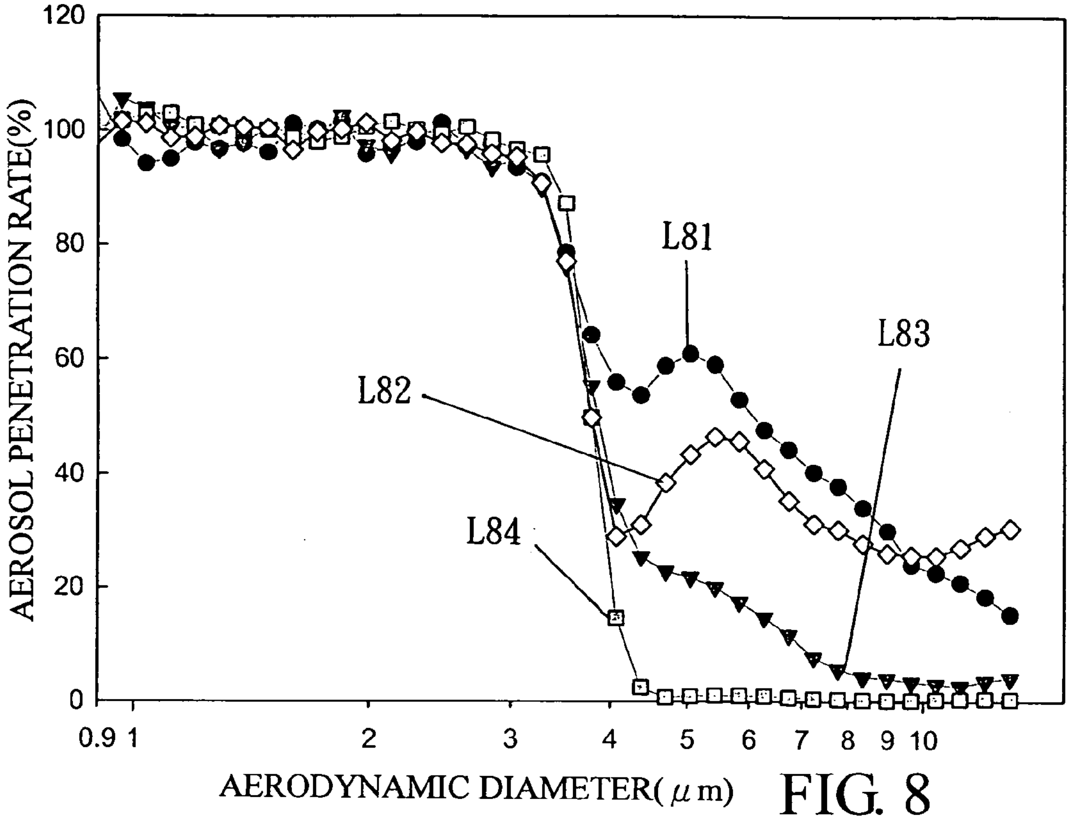
FIG. 8 is the first diagram of the experimental result of this invention.

According to FIG. 8, it can be found that the empty receiving cavity 12 cannot prevent the particle bounce phenomenon. Once the flat aluminum impaction plate 50 is coated with silicone oil 91, it can effectively avoid the solid PST particles bounce within a short period, but it cannot prevent such bounce for long time. In order to solve this particle bounce problem, a large amount of low-volatile oil (such as silicone oil 91) is filled in the receiving cavity 12. Because the low-volatile oil has a lower viscosity, this oil tends to leak out easily if the sampler is tilted, vibrating or shaking (such as the person with this sampler is walking). Thus, if the receiving cavity 12 is filled with the buffering layer 30 that is a semi-solid structure remaining a predetermined shape, it will be ideal solution for overcoming this particle bounce problem.

Figure 4G:
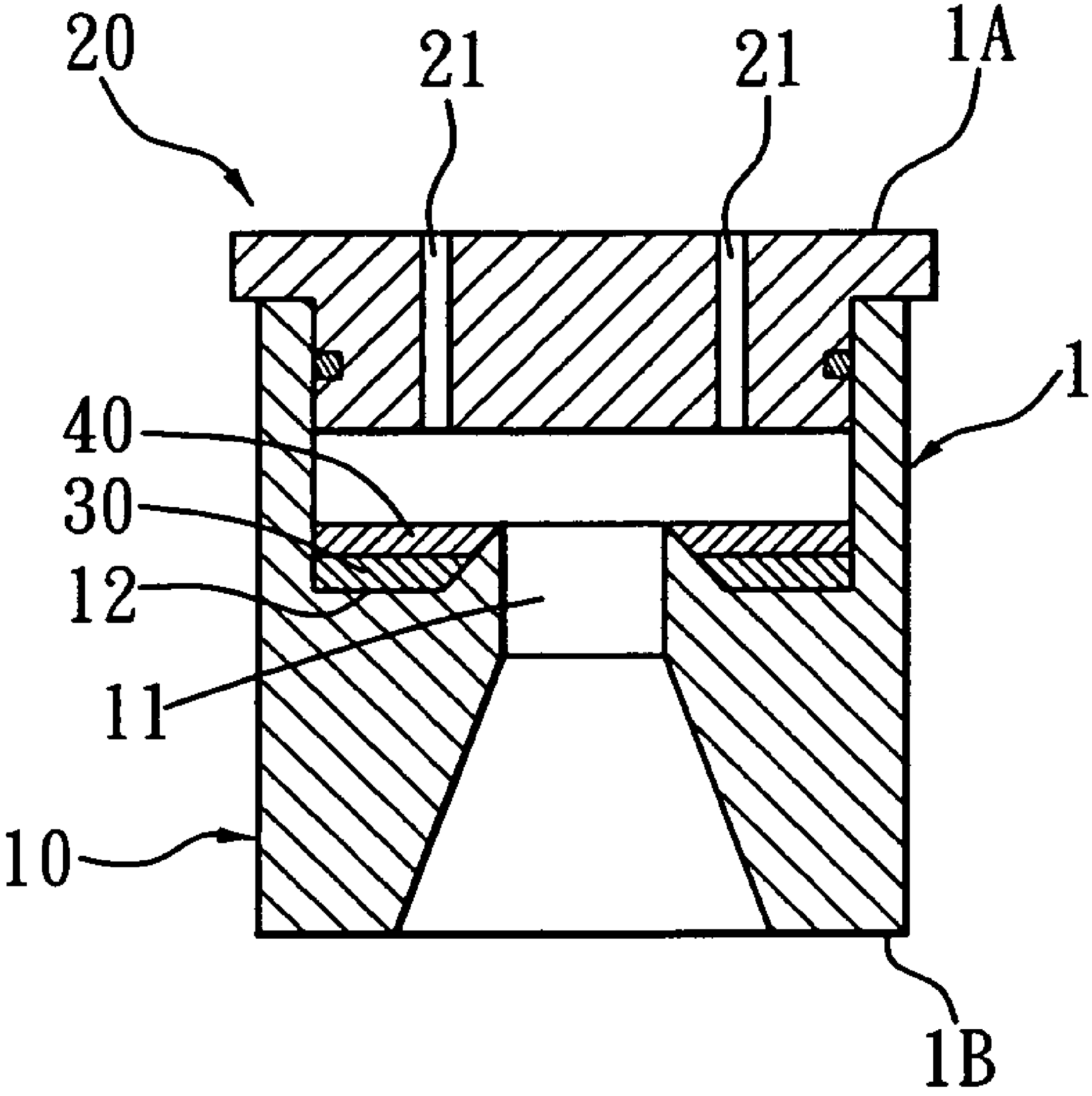
Figure 9:
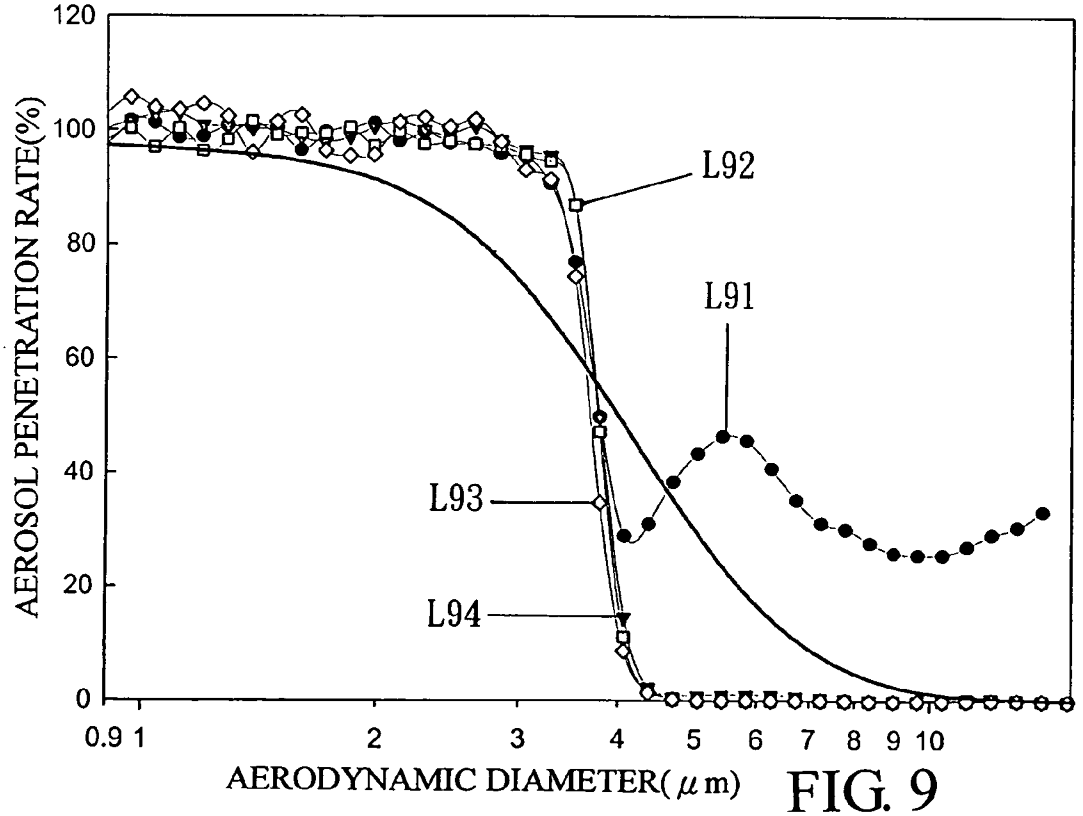
FIG. 9 is the second diagram of the experimental result of this invention.

As illustrated in FIG. 9, a six-holed multi-hole impaction plate is used for testing. The count medium diameter (briefly referred as CMD) of the challenge PST aerosols 92 is 5.86 μm, with the geometric standard deviation (briefly referred as GSD) of 1.56 (as shown in the curve L91 in FIG. 9). In addition, there are some liquid aerosols 92 of Dioctyl Phthalate (briefly referred as DOP) that is shown in the curve L92 in FIG. 9. Under the condition of the sampling flowing rate is 3.6 L/min, assume that the receiving cavity 12 is mounted with a flat aluminum impaction plate 50 or filled with 3% TSA (as shown in FIG. 4G; 3% TSA buffering layer 30 as shown in the curve L93 in FIG. 9) and coated with silicone oil 91 (as shown in FIG. 4D; and as shown in the curve L94 in FIG. 9). If comparing the particle bounce phenomenon of buffering layer 30 and the impaction plate 50, it can be found that both the flat aluminum impaction plate 50 coated with silicone oil 92 and the buffering layer 30 filled with 3% TSA can prevent the particle bounce within the initial short period (sampling time is 5 minutes). However, because the DOP is a liquid aerosol 92, no particle bounce occurs. So, in this experiment, it is just for comparison with others. In fact, this buffering layer 30 is directly filled in the receiving cavity 12.

Figure 10:
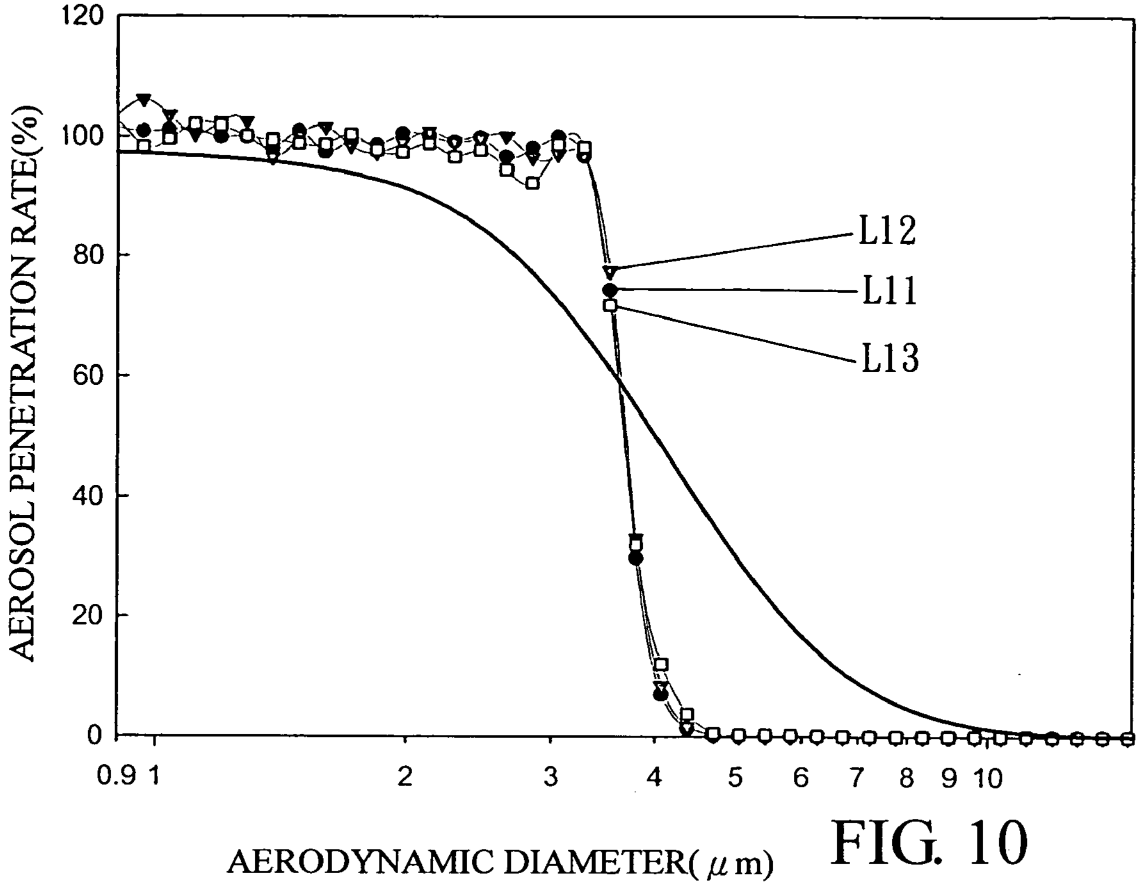
FIG. 10 is the third diagram of the experimental result of this invention.

However, the buffer layer 30 is used for substituting the impaction plate 50. It is very important to consider the ratio of the water inside. If there is too much water, the buffer layer 30 will be too fragile and cannot keep its original shape. If there is too little water, its structure becomes too hard and will be dried out quickly. It even could shrink. In this study, different percentages of water contained in the TSA (the buffering layer 30) are tested (such as 1%, 3%, and 6%). If it is over 6%, the TSA will be dehydrated our quickly and hard to prepared. The maximum percentage is kept at 6%. In FIG. 10, the experimental results include the curve L11 (for 1% TSA), curve L12 (for 3% TSA) and curve L13 (for 6% TSA). All these three cases can be used to prevent the particle bounce problem of the solid aerosols 92.

If the water contained in the TSA (buffering layer 30) is too little, its structure becomes too hard and will be dried out quickly. It even could shrink. Thus, it will influence the sampling efficiency. In view of the fact that the TSA is commonly prepared using hot water and released water, the long-term sampling of flowing air may promote this rigidity. A higher concentration of TSA considerably improves the discharge of water. In order to improve that, as shown in FIG. 4F, the 3% TSA (the buffering layer 30) is coated on a dehydration preventing layer 40 (such as silicone oil 91). So, it becomes a double-layered structure (the dehydration preventing layer 40 and buffering layer 30). Hence, it can reduce the drying condition on the TSA surface.

The American Conference of Governmental Industrial Hygienists (ACGIH) suggests that even biologically inert, insoluble inert, insoluble, or poorly soluble particles may have adverse effects and recommends that airborne concentrations should be kept below 3 mg/m$^3$, respirable particles, and 10 mg/m$^3$, inhalable particles, respectively. As illustrated in FIGS. 11A, 11B, 11C and 11D, it simulates a worse environment by generating the solid PST aerosols 92 with the mass concentration of 7.22 mg/m$^3$. Then, it can measure the long-term sampling effect for the one with TSA coating.

Figure 11A:
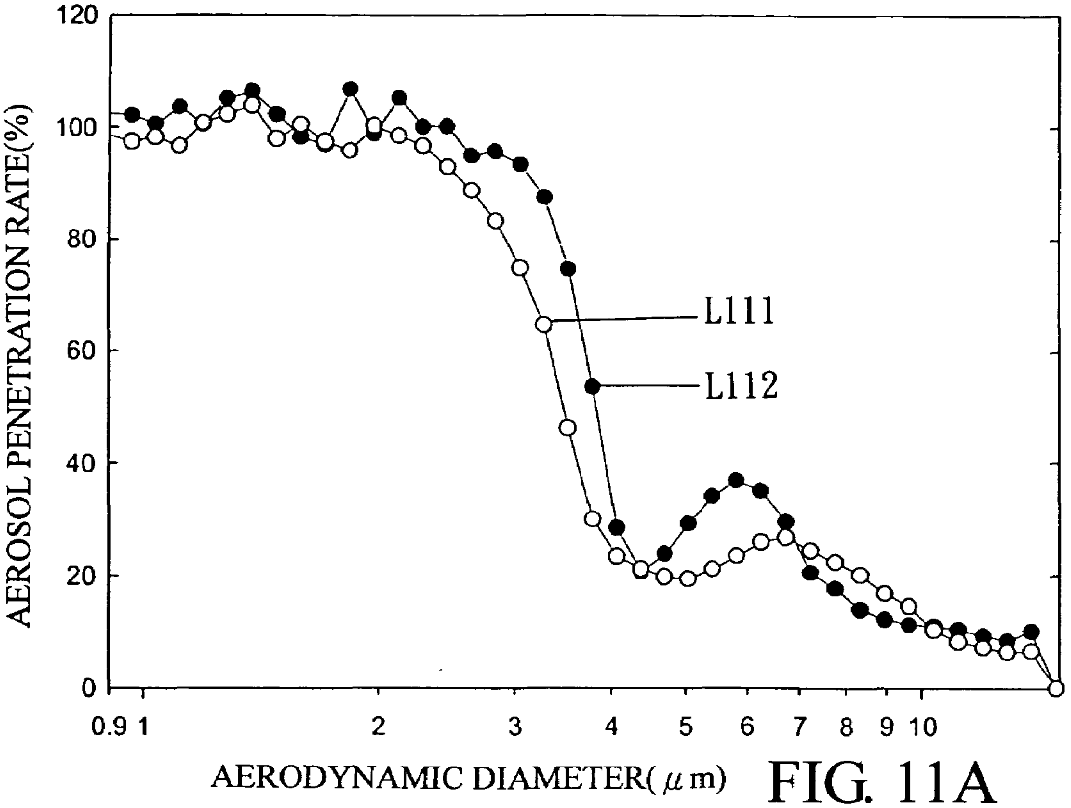
FIGS. 11A, 11B, 11C and 11D are the fourth diagrams of the experimental result at different stages within two hours.
Figure 11B:
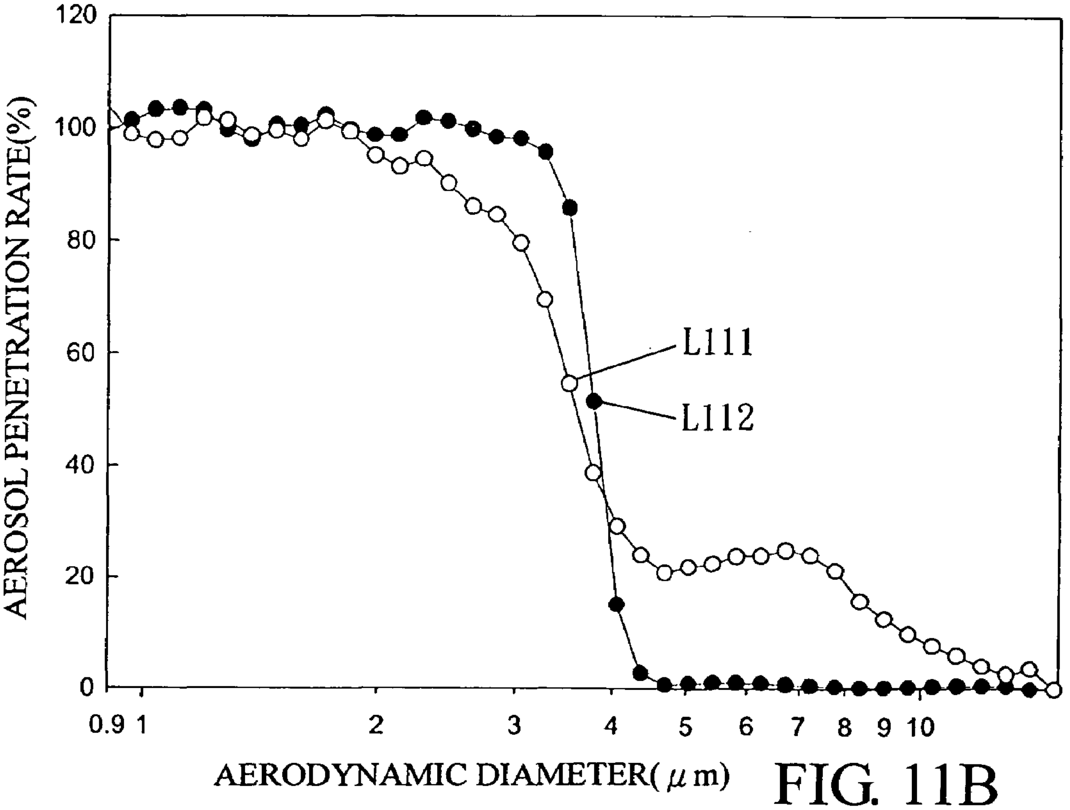
Figure 11C:
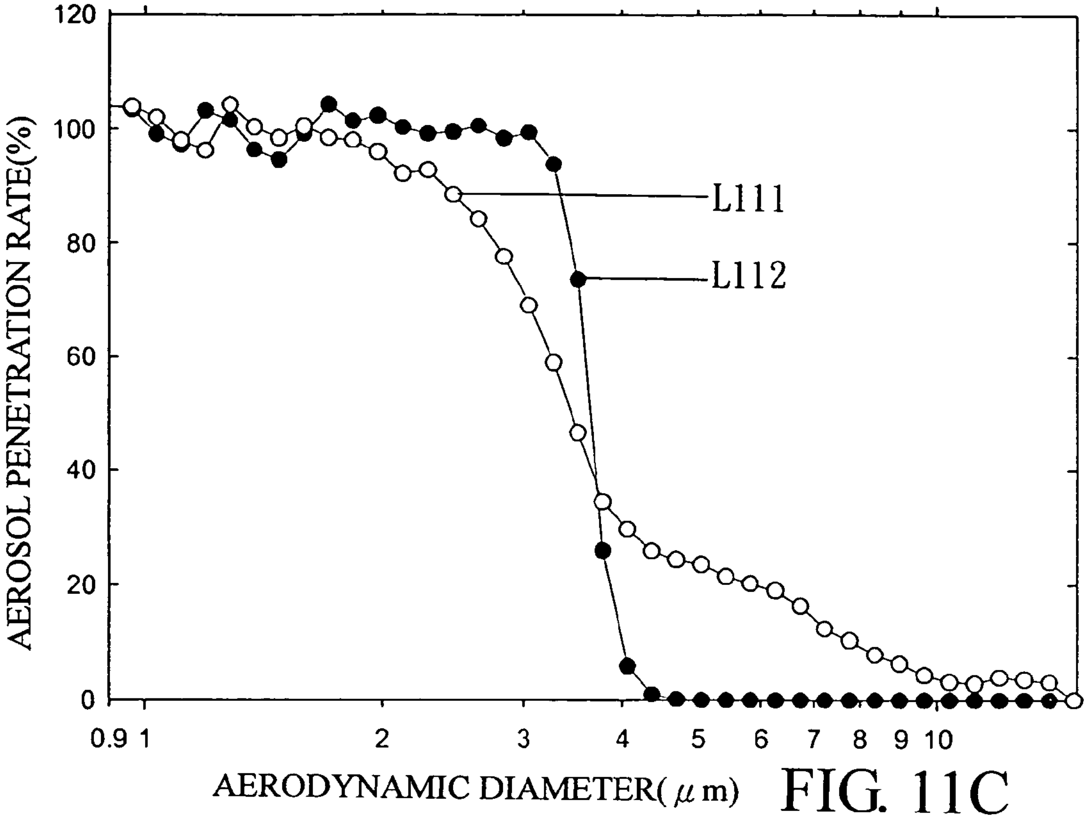
Figure 11D:
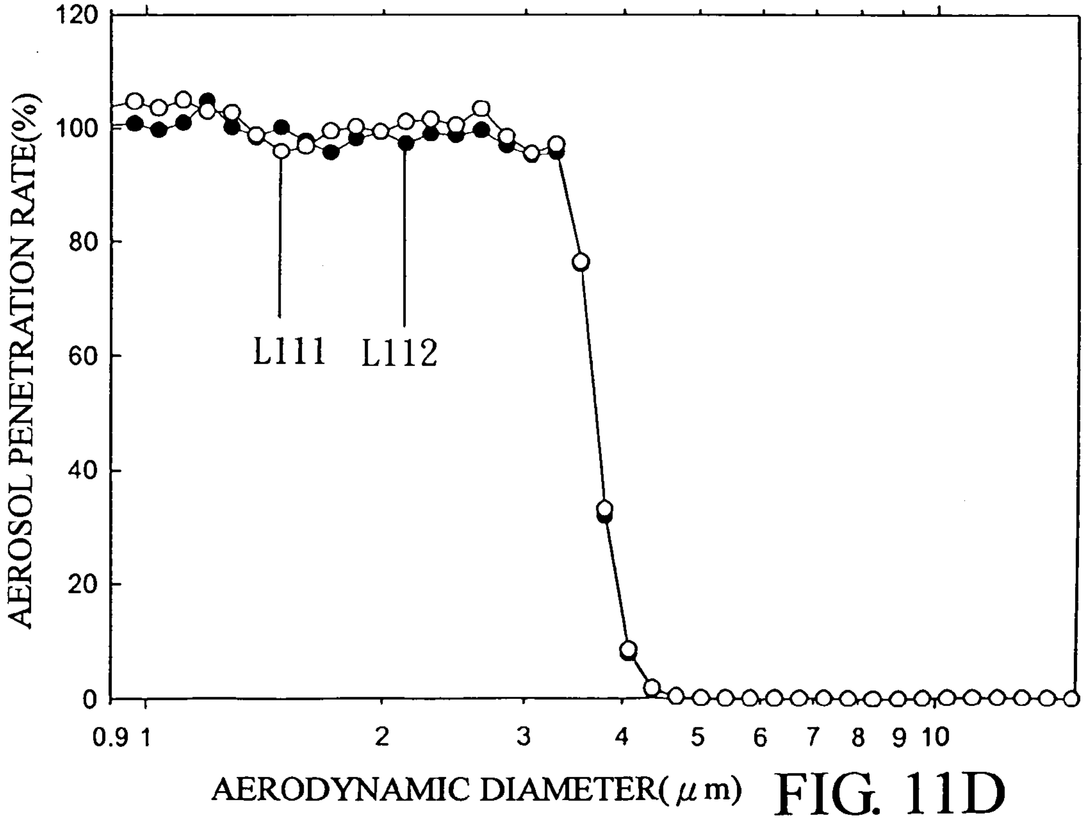

By using the porous impaction plate for testing, the CMD of challenge aerosols 92 is 5.86 μm and the mass concentration is around 3.6 L/min. One setting is to fill the 3% TSA (buffering layer 30) in the receiving cavity 12. The other setting is to use a general flat aluminum impaction plate 50. For both tests, a continuously particle loading is provided for two hours. Based on the result for the general flat aluminum impaction plate 50, it can found that it cannot avoid the particle bounce phenomenon for long time (as shown in FIG. 11A). Even though this general flat aluminum impaction plate 50 is coated with silicone oil 91, it still cannot minimize such particle bounce phenomenon for long time (as shown in FIG. 11B, the curve L112 is the initial sampling result; the curve L111 is the sampling result after two-hour particle loading). When the 3% TSA buffering layer 30 is filled, the particle bounce still happens because of the dehydration of TSA after two hours' sampling (as shown in FIG. 11C). However, once the double-layered structure (dehydration preventing layer 40 and the buffering layer 30) applies, such 3% TSA (buffering layer 30) can effectively prevent the particle bounce of the solid PST aerosols 92. Even after two-hour particle loading, their curves are quite consistent. Thus, this double-layered structure (dehydration preventing layer 40 and the buffering layer 30) really can yield the particle bounce of TST aerosols 92. In addition, it also can keep the shape of the 3% TSA buffering layer 30 and avoid the dehydration. Besides, by utilizing this receiving cavity 12, it also enhances the time for particle loading (as shown in FIG. 11D; the curve L112 shows the initial data; the curve L111 shows the sampling results after two hours). Indeed, its overall performance is significantly improved.

In addition, about the sampling data of the two-hour penetration rate, the aerosol penetration of 5 μm is selected for comparison and analysis. Because the amount of aerosol that had penetrated 5 μm was zero (see FIG. 10), if its penetration increases, it means the particle bounce (from the impaction plate 50 or from the buffering layer 30) occurs and can be perceived from the data.

Figure 12:
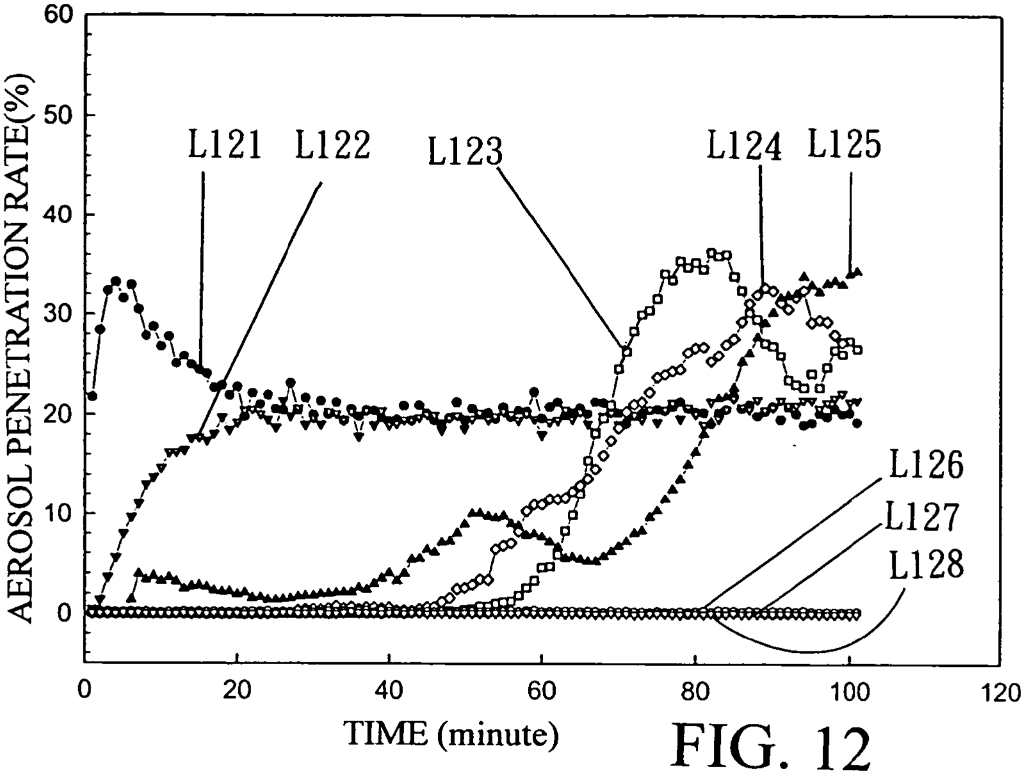
FIG. 12 is the fifth diagram of the experimental result of this invention.

As shown in FIG. 12, the sampling result of the flat aluminum impaction plate 50 without coating with the silicone oil 91 shows that the particle bounce occurs (as shown in the curve L121). Even though it is coated with silicone oil 91, the particle bounce occurs with a short period and becomes stable approximately after 20 minutes. This particle bounce makes the aerosol penetration becomes roughly 20%. It cannot prevent the particle bounce condition for long time.

As illustrated in FIG. 12, if the general flat aluminum impaction plate 50 is not coated with silicone oil 91 (as shown in the curve L121), the particle bounce problem occurs. Even though it is coated with silicone oil 91 (as shown in curve L122), the particle bounce still occurs after several minutes. Then, it remains stable after roughly 20 minutes. Meanwhile, its aerosol penetration rate is about 20% due to particle bounce. Anyway, it cannot prevent the particle bounce for long-term. If this impaction plate 50 is replaced by the buffering layer 30 which is 1% to 6% TSA, it still can not afford for long-term particle loading nor prevent the particle bounce of aerosols 92 for long time.

Figure 13:
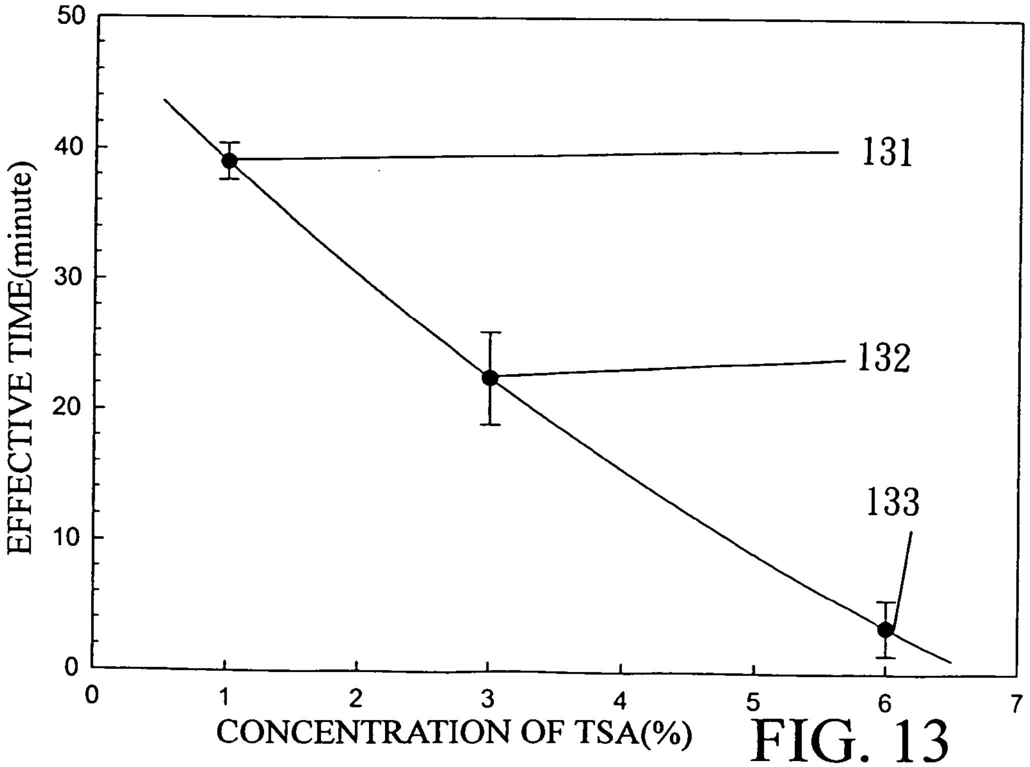
FIG. 13 is the sixth diagram of the experimental result of this invention.

As the TSA increases, the percentage of contained water will decrease and the structure will become harder. During the sampling process, it is easier to be dehydrated and shrunk. Therefore, it significantly decreases the collection efficiency for the solid PST aerosols 92. With regard to the relationship between the time for preventing the particle bounce and the concentration of TSA, it can be seen in FIG. 13. For 1% TSA (see the point 131), its effective time is about 40 minutes. For 3% TSA (see the point 132), its effective time is about 20 minutes. But, for 6% TSA (see the point 133), it effective time goes down to only 4 minutes.

When the 1%, 3% and 6% TSA buffer layers 30 are used, the results are as shown in the curves L123, L124, and L125. Furthermore, all of them are coated with silicone oil 91 respectively as their dehydration preventing layers 40; the results are shown in the curves L126, L127, and L128. The data prove that such double-layered structure, no matter for 1%, 3%, 6% TSA, can avoid the particle bounce of PST aerosols 92. Also, as the loading time passes, the aerosol penetration rate does not obviously increase. It means the design of doubled-layered structure filled in the receiving cavity 12 can yield the particle bounce effectively. Plus, it can improve the particle loading capacity for collecting the solid aerosols 92.

Figure 14:
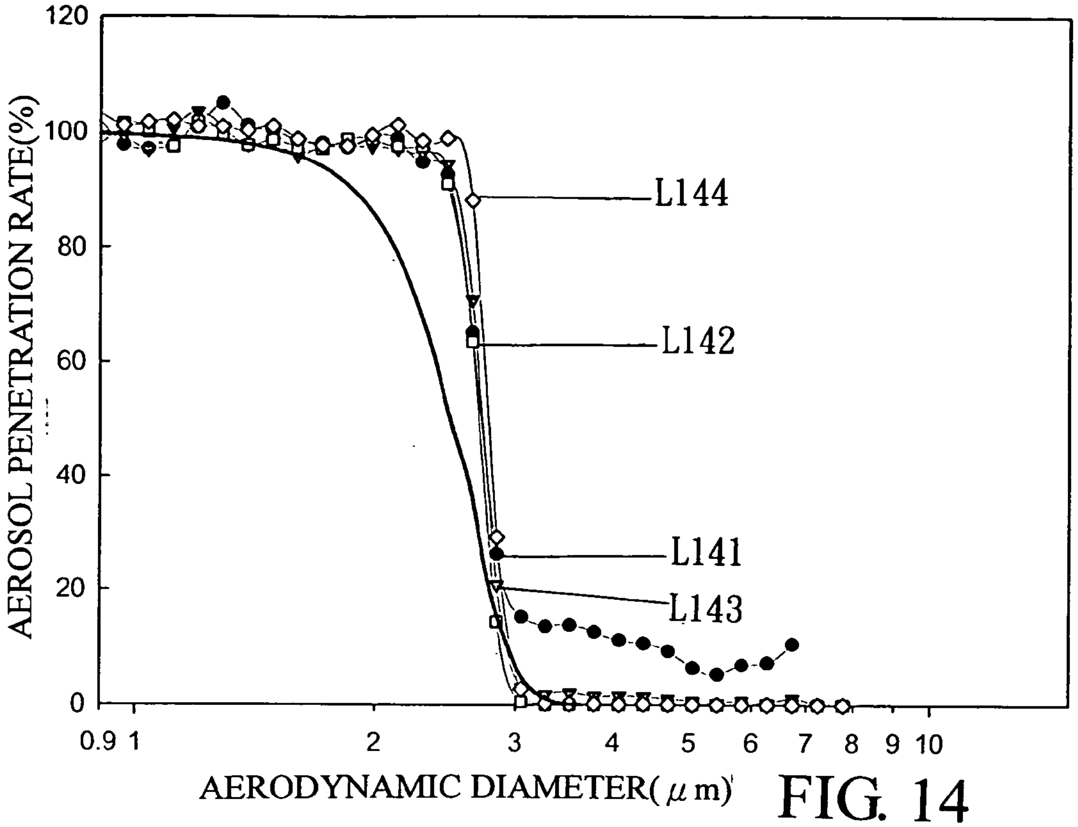
FIG. 14 is the seventh diagram of the experimental result of this invention.

As shown in FIG. 14, the CMD of challenge aerosols is 5.86 μm and the GSD of the PST is 1.56. The personal environmental monitor PM 2.5 (briefly called PEM-PM2.5 hereafter) with the flow rate of 10 L/min bought from the market is employed. At this experiment, the results for solid PST aerosols 92 (see the curve L141) and the liquid DOP aerosols 92 (see the curve L142) can be compared. Under the PEM-PM2.5 sampler, the traditional device utilizes the porous impaction plate 50 (there are many tiny holes and gaps inside the impaction plate 50) coated with a silicone oil 91 (see the curve L143) and this invention utilizes the double-layered structure which contains the dehydration preventing layer 40 and the buffering layer 30 (see the curve L144) are both tested for aerosol sampling.

The final results show the design of the double-layered structure which contains the dehydration preventing layer 40 and the buffering layer 30 is better than the design of traditional porous impaction plate 50. Also, it can be found that both the tradition porous impaction plate 50 coated with silicone oil and the one filled with 3% TSA as the buffering layer 30 can prevent the solid PST particle bounce in a short time, such as within 5 minutes.

Figure 15:
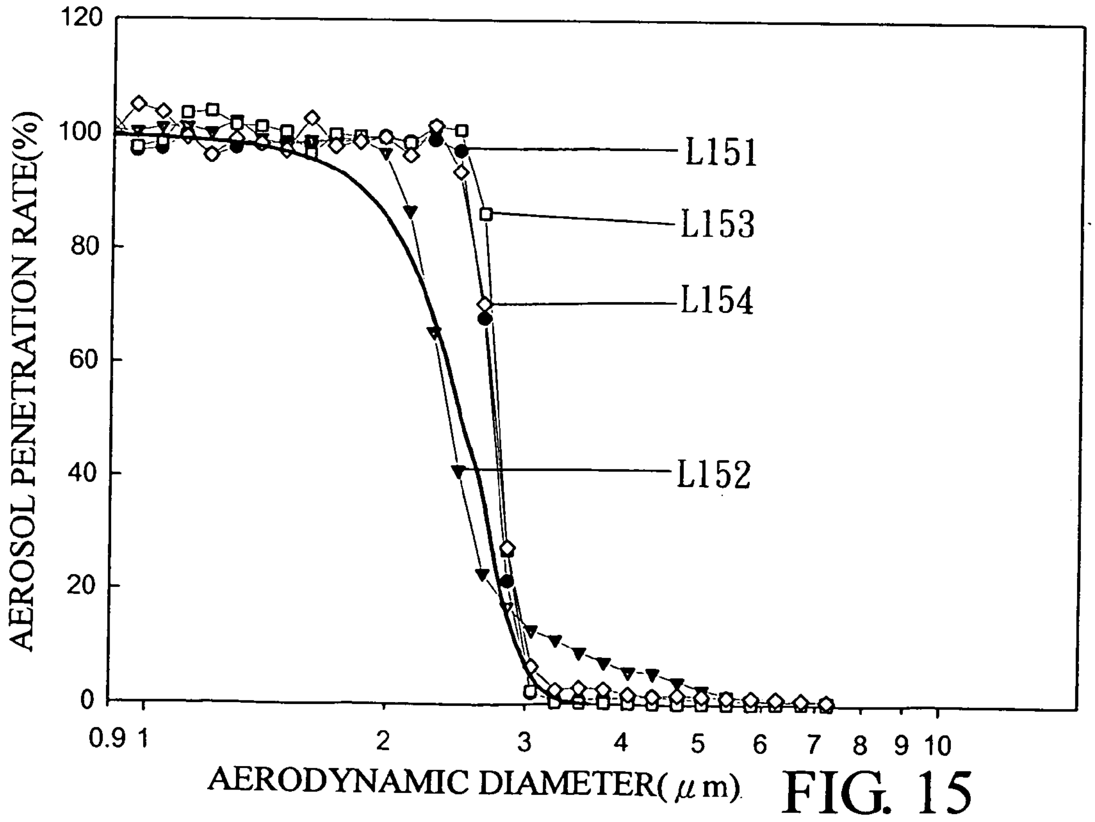
FIG. 15 is the eighth diagram of the experimental result of this invention.

Similarly, as shown in FIG. 15, if the mass concentration of the solid aerosols 92 is 7.22 mg/$m^3$ for long-term (about two hours) particle loading, it can avoid the particle bounce. Because the one with 3% TSA will gradually be dried and shrunk, it cannot avoid the particle bounce after two hours.

However, if the double-layered structure (which contains the dehydration preventing layer 40 and the buffering layer 30) filled in the receiving cavity 12 is applied, it can avoid the particle bounce. The aerosol penetration rate remains constant at the initial stage (as shown in curve L153) and the two-hour-later stage (as shown in the curve L154). Obviously, the double-layered structure (which contains the dehydration preventing layer 40 and the buffering layer 30) filled in the receiving cavity 12 can be applied to the PEM-PM2.5 sampler. It can yield the particle bounce of PST aerosols 92 and can prolong the loading time for aerosols 92 sampling.

The advantages and functions of the present invention can be summarized as follows:

[1] Its accuracy is high. By utilizing the unique design of the buffering layer and the dehydration preventing layer, the present invention can significantly avoid the particle bounce phenomenon during the aerosol sampling process. Furthermore, it reduces the sampling bias of the collected weight caused by particle bounce. So, its accuracy can be raised significantly.

[2] Its sampling time lasts longer. Because the particle loading capacity of this invention is larger, its sampling time lasts longer. Meanwhile, it not only can precisely evaluate the density of the hazardous aerosol in the air, but also can accurately measure the condition that a worker exposes in such environment containing hazardous particles for a worker in the air.

[3] It can endure vibrations. This invention has a circularly and downwardly receiving cavity. Thus, it is easy to fill in a semi-solid material that is soluble to water and can remain its shape. Because it is not easy to be move away or leak out due to tilting it can endure vibrations.

[4] It can prevent the particle bounce effect. By using the circularly and downwardly receiving cavity, the filled buffering layer can receive these hitting particles and make them solute to water inside the layer. Thus, it can yield the particle bounce effect.

[5] Its cost is low. About this buffering layer, if the manufacturer chooses the Trypticase Soy Agar (TSA) as the buffering layer, it is available in the market and low-priced. So, the total cost of this invention is low.

[6] Its application scope is wide. In the world, there are many commonly-used impactors, such as Harvard Impactor, Dichotomous Sampler, PM10 (Personal Environmental Monitor-PM10, PEM-PM10), Hi-vol Sampler, Micro-Orifice Uniform Deposit Impactor (briefly called MOUDI), Airborne Particulate<PM-10>Monitor, TEOM series 1440*a*, and so on. All these impactor utilized the same principle. If this invention applies, the accuracy for sampling and data analysis can be significantly improved.

The above embodiments are only used to illustrate the present invention, not intended to limit the scope thereof. Many modifications of the above embodiments can be made without departing from the spirit of the present invention.

What is claimed is:

1. An aerosol size-selective impactor for reducing particle bounce, comprising:

a main structure, said main structure including a base and a nozzle plate that fit on said base, said nozzle plate having at least one nozzle thereon, said main structure having an inlet and an outlet, said main structure being disposed with a central channel and a receiving cavity, said central channel and a receiving cavity being disposed on said base, said central channel having a conically shaped lower portion, said inlet being disposed with at least one nozzle;

at least one buffering layer being installed in said receiving cavity, said buffering layer containing water and being a semi-solid structure maintaining a predetermined shape; and a dehydration preventing layer coated on said buffering layer for reducing a drying phenomenon of said buffering layer.

2. The aerosol size-selective impactor for reducing particle bounce as claimed in claim 1, wherein said buffering layer includes a material selected from one of the group consisting of Trypticase Soy Agar (TSA), Agar that contains water, glue, solid water-soluble material, and grease that contains water, low-volatile oil that contains water; said dehydration preventing layer being selected from one of the group consisting of silicone oil, low-volatile oil, low-volatile grease, and chemical material for preventing dehydration.

* * * * *